United States Patent [19]

Müller-Berghaus et al.

[11] Patent Number: 6,143,179
[45] Date of Patent: Nov. 7, 2000

[54] METHOD FOR THE AFFINITY-CHROMATOGRAPHIC PURIFICATION OF FACTOR VIII

[75] Inventors: Gert Müller-Berghaus, Ober-Mörlen; Bernd Pötzsch, Giessen; Horst Schwinn, Mainz, all of Germany

[73] Assignee: Kerckhoff-Klinik GmbH, Munich, Germany

[21] Appl. No.: 09/202,800

[22] PCT Filed: Jun. 24, 1996

[86] PCT No.: PCT/EP96/02746

§ 371 Date: Dec. 22, 1998

§ 102(e) Date: Dec. 22, 1998

[87] PCT Pub. No.: WO97/49730

PCT Pub. Date: Dec. 31, 1997

[51] Int. Cl.[7] .................................................. B01D 15/08
[52] U.S. Cl. ...................... 210/635; 210/656; 210/198.2; 210/502.1; 530/383; 530/413
[58] Field of Search ................................... 210/635, 656, 210/659, 198.2, 502.1; 530/383, 413, 417

[56] References Cited

U.S. PATENT DOCUMENTS

| | | | |
|---|---|---|---|
| 4,877,614 | 10/1989 | Andersson | 530/383 |
| 4,965,199 | 10/1990 | Capon | 530/383 |
| 5,252,709 | 10/1993 | Burnout | 530/383 |
| 5,543,502 | 8/1996 | Nord Fang | 530/383 |
| 5,605,884 | 2/1997 | Lee | 530/383 |
| 5,633,150 | 5/1997 | Wood | 530/383 |
| 5,668,108 | 9/1997 | Capon | 530/383 |

FOREIGN PATENT DOCUMENTS

| | | | |
|---|---|---|---|
| 295645 | 6/1988 | European Pat. Off. | 530/383 |
| 195 21 313 A1 | 12/1996 | Germany | 530/383 |

OTHER PUBLICATIONS

Knutson, et al., "Porcine Factor VII:C Prepared By Affinity Interaction With Von Willebrand Factor and Heterologous Antibodies Sodium Dodecyl Sulfate Poly Acrylomide Gel Analysis," Blood 59(3):615–624 (1982) (computer generated abstract).

Primary Examiner—Ernest G. Therkorn

[57] ABSTRACT

The invention concerns a process for the purification of factor VIII by affinity chromatography characterized in that a biological fluid containing factor VIII is contacted with immobilized cellular von Willebrand factor or a derivative thereof under such conditions that factor VIII is adsorbed to the immobilized von Willebrand factor or derivative thereof, impurities are separated and adsorbed factor VIII is eluted.

19 Claims, No Drawings

METHOD FOR THE AFFINITY-CHROMATOGRAPHIC PURIFICATION OF FACTOR VIII

This application is a 371 of International Application No. PCT/EP96/02746, filed Jun. 24, 1996.

DESCRIPTION

The present invention concerns a process for the affinity chromatographic purification of factor VIII by adsorption to immobilized von Willebrand factor.

The purification of human factor VIII (FVIII) from biological fluids such as plasma, plasma fractions or plasma derivatives using affinity chromatographic methods has been known for a long time.

Thus Tuddenham et al. (J. Lab. Clin. Med. 93 (1979), 40–53) describe such a purification procedure using immobilized polyclonal antibodies which were isolated from the plasma of inhibitor patients.

Veerman E. C. I. et al. (Thromb. Res. 33 (1983), 89–93) describe a purification process using monoclonal antibodies to human FVIII.

Furthermore processes for the purification of FVIII are known using immobilized monoclonal murine antibodies to human von Willebrand factor (vWF) in which vWF/FVIII complexes are adsorbed and subsequently vWF-free FVIII is isolated by known methods (cf. e.g. EP-A-0083 438 and U.S. Pat. No. 4,831,118).

However, a disadvantage of these processes is that separation of FVIII from its natural stabilizer, the vWF, has an adverse effect on the stability of FVIII. Moreover it is unfavourable for certain forms of therapy to obtain a completely vWF-free FVIII preparation (Hornsey et al, Thromb. Haemost. 57 (1987), 102–105).

Adsorption of FVIII to immobilized plasmatic vWF is already known (cf. Leyte et al., Biochem. J. 257 (1989), 679–683). However, it was found that only about 1–2% of the plasmatic FVIII activity is bound to immobilized plasmatic vWF. An economic process is inconceivable with such a result.

Hence an object of the present invention was at least to partially eliminate the disadvantages of the state of the art. In particular a process should be provided which enables a high purification efficiency to be obtained in a simple and cost-effective manner.

This object is achieved by a process for the purification of factor VIII by affinity chromatography characterized in that a biological fluid containing factor VIII is contacted with immobilized cellular von Willebrand factor or a derivative thereof under such conditions that factor VIII is adsorbed to the immobilized von Willebrand factor or derivative thereof, impurities are separated and adsorbed factor VIII is eluted. It was surprisingly found that cellular vWF e.g. vWF formed by endothelial cells is, in contrast to plasmatic vWF, excellently suitable after immobilization for purifying FVIII. A vWF produced by endothelial cells (EC-vWF) has namely a substantially higher affinity for FVIII than plasmatic vWF so that it is possible to isolate the FVIII activity from biological fluids in high purity and yield.

Cellular vWF is preferably isolated from cultured human cells, preferably from cultured human endothelial cells e.g. from human endothelial cells of the umbilical vein (HUVEC), bound to the solid phase and incubated with a biological fluid. After separation of impurities (non-binding or unspecifically-binding impurities), the adsorbed FVIII is eluted preferably by applying a salt gradient. The advantages of the process according to the invention are in particular that human material is used exclusively, the purification is less time consuming and the purified FVIII has a low proteolysis rate. This leads to an unusually high specificity of the purified material.

Human plasma, plasma fractions, plasma derivatives e.g. cryoprecipitates or culture supernatants of cells producing FVIII are preferably used as biological fluids. The biological fluid can optionally be subjected to a prior chromatographic purification e.g. an aluminium hydroxide adsorption.

If plasma is used as the biological fluid, a predilution of ca. 1:2 and the addition of proteinase inhibitors is preferred.

It is additionally preferred to keep the biological fluid containing FVIII in contact with the immobilized vWF for a period of at least 30 min. A contact period of at least 1 h is particularly preferred. The incubation temperature is preferably 10 to 37° C.

Monomeric vWF or derivatives thereof e.g. dimeric, oligomeric or multimeric vWF or peptides with FVIII-binding properties which can be prepared from such vWF fractions can be used as immobilized VWF.

The vWF or the derivative thereof is immobilized on an inert, preferably particulate carrier material. Examples of suitable carrier materials are inorganic carriers such as silica gel, silicates, porous glasses or organic carrier materials such as optionally cross-linked polysaccharides e.g. cellulose, cellulose derivatives, dextrans or optionally modified agarose. A preferred carrier is Sepharose®, a material based on modified agarose whose polysaccharide chains are linked to form a three-dimensional network.

After adsorption of FVIII from the biological fluid to the immobilized vWF, the biological fluid is separated. Before the elution a further wash process is preferably carried out in order to remove components such as plasma proteins that are bound unspecifically to the carrier.

The subsequent elution is preferably achieved by increasing the ionic strength e.g. by applying a gradient with an increasing salt concentration. An NaCl gradient of 0.6–1.5 M has proven to be particularly suitable.

The biological fluid containing FVIII that is contacted with the immobilized carrier preferably has a pH value of 6.4–7.2, particularly preferably a pH value of ca. 6.8. In addition it is preferable to add hirudin to the biological fluid and optionally to the wash solution.

The process according to the invention enables at least 50% and particularly preferably at least 70% of the FVIII activity to be isolated from the biological fluid.

In addition an FVIII preparation is obtained by the process according to the invention with a high purity of preferably at least 50 IU/mg protein e.g. ca. 100 IU/mg protein.

Yet a further advantage of the process according to the invention is that an FVIII preparation is obtained which additionally contains still complexed vWF. The preparation preferably contains 1 U vWF per 5–15 IU FVIII. An IU for FVIII and vWF is defined in Bloom et al., Haemostasis and Thrombosis, 3rd edition, Churchill Livingstone, Edinburgh, 1994.

The preparation containing VWF-FVIII purified by the process according to the invention can subsequently be subjected to one or several known processes for virus inactivation (e.g. EP-A-0 131 740 and PCT/EP94/00328).

The process according to the invention is further elucidated by the following example.

EXAMPLE 1

A process is described which is suitable for purifying FVIII from human plasma or plasma derivatives. The basis of the method is the different binding affinity of plasmatic and endothelial vWF to FVIII. Endothelial vWF (EC-vWF)

is isolated from cultured human endothelial cells of the umbilical vein (HUVEC), bound to a solid phase and incubated with plasma. After removing unspecifically bound plasma proteins, the bound FVIII is isolated with a salt gradient.

1.1 Isolation and Preparation of the EC-VWF Matrix

EC-VWF is isolated from the supernatant of cultured HUVEC in the second and third passage. For this the cells are cultured in culture dishes with a diameter of 150 mm, washed with 37° C. warm phosphate-buffered salt solution (PBS) after reaching confluence and subsequently stimulated with PMA, a phorbol ester. This stimulation leads to the release of intracellular vWF into the culture supernatant. The isolated supernatants are pooled, the EC-VWF is purified and adjusted to a final concentration of 2–5 mg/ml. After dialysis against a sodium hydrogen carbonate buffer (0.1 M, pH 8.3), the EC-VWF is coupled to CNBr-activated Sepharose 4B (Pharmacia) according to the manufacturer's instructions. 1 M glycine is used to saturate unspecific binding sites. The EC-vWF-Sepharose can be stored until use in TBS, 0.01% thimerosal.

1.2 Adsorption of FVIII to Immobilized vWF

A suitable starting material is example plasma anticoagulated with sodium citrate, cryoprecipitate isolated from this plasma or another plasma derivative. The cryoprecipitate can be initially subjected to an aluminium hydroxide adsorption (2% (v/v) aluminium hydroxide (Calbiochem, USA), 20 min room temperature, 10,000 g centrifugation) and diluted in a ratio of 1:2 with 50 ml application buffer (100 mM NaCl, 50 mM Tris, 80 mM calcium chloride, 100 ng r-hirudin, pH 6.8). Then the cryo/buffer mixture is centrifuged at 10,000×g for 30 min at room temperature. Even when using plasma it is preferable to predilute by 1:2. The prepared sample can be incubated with the EC-vWF-Sepharose in a closed vessel as well as in an open chromatography device. Before starting the elution, the column matrix is washed with 10 column volumes of TBS (500 mM NaCl, 20 mM Tris-HCl, 50 ng r-hirudin).

1.3 Elution of the Bound FVIII

The elution is carried out with a continuous gradient of 0.6–1.5 M NaCl in 20 mM Tris-HCl, 150 mM $MgCl_2$, pH 6.8. Samples containing FVIII are pooled, dialysed against PBS, pH 6.8 and stored at −80° C. preferably after addition of 0.1% human serum albumin (HSA). Storage is possible up to at least 6 months without loss of activity.

1.4 Example of a Typical Purification

A commercially available cryoprecipitate was thawed at 37° C., subjected to an aluminium hydroxide adsorption as already described and diluted in a ratio of 1:2 with application buffer. Three independent purifications each using the same column were carried out on 20 ml aliquots of this material.

| Fraction | Protein (mg) | vWF antigen (µg) | FVIII activity (IU) | FVIII-ag (ng) | FVIII act. protein ratio |
|---|---|---|---|---|---|
| starting material | 27 | 284 | 117 | 783 | 4.3 |
| eluate 1 | 1.46 | 57 | 72 | 694 | 49 |
| eluate 2 | 0.91 | 47 | 89 | 673 | 97 |
| eluate 3 | 1.08 | 45 | 78 | 564 | 72.2 |

After each purification the EC-VWF matrix was washed with a 1 M NaCl solution (five column volumes) for regeneration, to remove contaminating proteins and subsequently washed with TBS. Storage in this buffer is possible after adding 0.01% thimerosal. The matrix should be intensively washed with application buffer before use.

We claim:

1. A process for the purification of factor VIII by affinity chromatography, comprising contacting a biological fluid containing factor VIII with immobilized, cellular von Willebrand factor or a derivative thereof, under conditions such that factor VIII is adsorbed to said immobilized, cellular von Willebrand factor or to the derivative thereof, separating impurities therefrom and eluting adsorbed factor VIII from said immobilized, cellular von Willebrand factor.

2. The process of claim 1, wherein said biological fluid is human plasma, a plasma fraction, a plasma derivative or a culture supernatant of a cell which produces factor VIII.

3. The process of claim 1, wherein said biological fluid is a human plasma cryoprecipitate.

4. The process of claim 1, comprising subjecting said biological fluid to chromatographic purification with aluminum hydroxide prior to contact with said immobilized, cellular von Willebrand factor.

5. The process of claim 1, wherein said immobilized, cellular von Willebrand factor or derivative thereof is from endothelial cells.

6. The process of claim 1, wherein said cellular von Willebrand factor or derivative thereof is immobilized on particulate, carrier material.

7. The process of claim 1 wherein the carrier material is silica gel, a silicate, a porous glass or a polysaccharide.

8. The process of claim 1, comprising keeping said biological fluid in contact with said immobilized cellular von Willebrand factor for at least 30 minutes.

9. The process of claim 8, comprising contacting said biological fluid with said immobilized, cellular von Willebrand factor for at least 1 hour.

10. The process of claim 1 comprising washing said factor VIII before elution.

11. The process of claim 1, comprising eluting factor VIII by increasing ionic strength of an eluting agent.

12. The process of claim 11, comprising applying a gradient of increasing salt concentration.

13. The process of claim 1, wherein said biological fluid has a pH of from 6.4 to 7.2.

14. The process of claim 1, comprising adding hirudin to said biological fluid.

15. The process of claim 1 comprising isolating at least 50% of factor VIII activity from said biological fluid.

16. The process of claim 1 comprising obtaining a factor VIII preparation with a purity of at least 50 IU/mg protein.

17. The process of claim 1, comprising obtaining a factor VIII preparation which contains complexed von Willebrand factor.

18. The process of claim 17, wherein said preparation contains 1 U von Willebrand factor per 5–15 IU factor VIII.

19. The process of claim 1, further comprising subjecting said factor VIII to a process to inactivate viruses.

* * * * *